(12) United States Patent
Singh et al.

(10) Patent No.: US 6,939,718 B2
(45) Date of Patent: Sep. 6, 2005

(54) MASS SPECTROMETRY OF PROSTAGLANDINS

(75) Inventors: Rajendra Singh, San Jose, CA (US); Halhong Zhou, Mountain View, CA (US)

(73) Assignee: SurroMed, LLC, Wilmington, NC (US)

(*) Notice: Subject to any disclaimer, the term of this patent is extended or adjusted under 35 U.S.C. 154(b) by 35 days.

(21) Appl. No.: 10/044,310

(22) Filed: Jan. 11, 2002

(65) Prior Publication Data

US 2002/0146838 A1 Oct. 10, 2002

Related U.S. Application Data

(60) Provisional application No. 60/261,577, filed on Jan. 12, 2001.

(51) Int. Cl.[7] .............................................. G01N 33/00
(52) U.S. Cl. ...................................... 436/129; 436/173
(58) Field of Search .................................. 436/129, 173

(56) References Cited

U.S. PATENT DOCUMENTS

5,015,848 A * 5/1991 Bomse et al. ................ 250/281

OTHER PUBLICATIONS

Kamel et al. "Effect of Mobile–Phase Additives, Solution pH, Ionization Constant, and Analyte Concentration on the Sensitivities and Electrospray Ionization Mass Spectra of Nucleoside Antiviral Agents", Anal. Chem., 1999, v. 71, pp. 5481–5492.*

Technical Note: CE–ESI–MS: An Integrated Solutions: http://www.ceandcec.com/59681328.pdf, Jan. 11, 2000.*

Ahn et al. "Efficient Analysis of Oligosaccharide–Malononitrile Derivatives by On–line Capillary Liquid Chromatography/Electrospray Ionization Mass Spectrometry", Rapid Comm. Mass Spectrom., 1999, v. 13, pp. 855–859.*

Watkins et al. "Synthesis of of 8–epi–prostaglndin F2a iby human endothelial cells: role of prostglandin H2 synthase", Biochem. J., 1999, v. 344, pp. 747–754.*

Newby et al. "Rapid simultaneous analysis of prostaglandin E2, 12–hydroxyeicosatetraenoic acid and arachidonic acid using HPLC/electrospray ionization mass spectrometry", Rapid Commun. Mass Spectromet (1997), 11(15), 1723–1727.*

Schilling et al. "Ammonia (NH3 and N2H3) direct chemical ionization mass spectrometry of underivatized prostaglandin–H2 an other selected stable prostaglandins", Biomedical & Environmental Mass Spectrometry (1986), 13(10), 545–51, Abstract.*

Margalit et al. : "Rapid quantitation of a large scope of eicosanoids in two models of inflammation: development of an electrospray and tandem mass spectrometry method and application to biological studies" Anal. Biochem. (1996), 235(1), 73–8.*

(Continued)

*Primary Examiner*—Yelena G. Gakh
(74) *Attorney, Agent, or Firm*—Sheridan Ross P.C.

(57) ABSTRACT

A liquid chromatography-electrospray ionization mass spectrometry method is capable of separating and identifying different prostaglandin isomers, including $PGD_2$ and $PGE_2$. Unlike traditional gas chromatography methods, little sample preparation and no derivatization are required. The chromatography is performed under acidic conditions that are optimal for separating the isomers. A basic sheath flow liquid is added to the chromatographic eluent, resulting in high ionization efficiency when the electrospray ionization is performed in negative ion mode. Additionally, by altering the energy at which the ionization is performed, tandem mass spectra of the two isomers can be made to differ as a result of the different relative energies of the two isomers.

23 Claims, 8 Drawing Sheets

OTHER PUBLICATIONS

Ballard et al. "Sequential product–ion spectra (MS3 and MS4) with array detection and reaction–intermediate scanning on a fou sector mass spectrometer", Rapid Communications in Mass Spectrometry (1992), 6(9), 553–9, Abstract.*

Kanai et al. "HPLC–ESI/ion trap mass spectrometer system for structural analysis of biomolecules".*

Bose et al. "Mass spectral studies. VIII. Some aspects of chemical ionization mass spectroscopy using ammonia as reagent gas: a valuable technique for biomedical and natural products studies"; Anal. Biochem., 1978, 89 (1) 284–291.*

Traitler et al. "Derivatization and internal standardization in prostanoid analysis", Colloque INSERM (1987), 152(Biol. Icosanoids Prod. Apparentes Niveau Cell. Sang. Vasc.) 129–42, Abstract.*

Strife et al. "Tandem mass spectrometry of prostaglandins: a comparison of an ion trap and a reserved geometry sector instrument", Rapid Communications in Mass Spectrometry (1988), 2(6), 105–9.*

Takabatake et al. "Simultaneous quantification of prostaglandins in human synovial cell–cultured medium using liquid chromatography/tandem mass spectrometry"; Prostaglandins, Leukotrienes and Essential Fatty Acids (2002), 67(1), 51–56.*

Yang et al. "Quantitative high–performance liquid chromatography/electrospray ionization tandem mass spectrometric analysis 2– and 3–series prostaglandins in cultured tumor cells" Analytical Biochemistry (2002), 308(1), 168–177t al.*

Singh et al. (2001) 14th International Symposium of Microscale Separations and Analysis.

Gillespie et al. (1990) J Am Soc Mass Spectrom 1, 389–396, "Differences in the Low–Energy Collison–Activated Dissociation of Carboxylate Anions from Structurally Similar Prostaglandins: E2, F2α, D2, and DHKF2α".

Li et al., (Nov. 1999) Proc. Natl. Acad. Sci. 96:13381–13386, "Quantitative high performance liquid chromatography/tandem mass spectrometric analysis of the four classes of F2–isoprostanes in human urine."

Abian (1988) Biomed. Environ. Mass Spectrom. 16(1–12):215–219 Abstract.

Lawson et al. (1998) J. Biol. Chem. 273(45):29295–29301.

Kempen et al. (2001) Anal. Biochem. 297:183–201 Abstract.

Abián et al. Biomedical and Environmental Mass Spectrometry, 16:215–219 (1988).

Pace–Asciak, et al. "Gas chromatographic–mass spectrometric profiling with negative–ion chemical ionization of prostaglandin and their 15–keto– 13,14–dihydro catabolites in rat blood", J. Chromatogr., 1984, v. 310 (2), pp. 233–42, Abstract.

Adachi et al., "Characterization of prostaglandin by LC/APCI–MS", Bunseki Kagaku, 1994, 43 (3), pp. 189–194, Abstract.

Obata, et al., "Simultaneous quantitative analysis of prostaglandin by GC/MS for cell characterization", Nippon Iyo Masu Supekutoru Gakkai Koenshu, 1995, 20, pp. 89–92, Abstract.

Eling et al., (1982) Methods in Enzymology 86:511–517.

Roberts & Morrow, (1997) Biochem. Biophys Acta. 1345:121–135.

Tsikas et al. (1998) J. Chromatgr. B 717:201–245.

Tsikas et al., (1998) J. Chromatogr. B 716:7–17.

Wang et al., (1995) J. Pharmacol. Exp. Ther. 275:94–100.

Whorton et al., (1979) J. Chromatogr. 163:64–71.

* cited by examiner

```
Magic Temperature Controller
     Temperature: 40

Magic Pump
     Run time: 60.00 min
     Initial Valve Position: INJECT
     Pump A: Enabled
     Pump B: Enabled Time Program
     time:  0.00  flow 45.00   %b: 26.00
     time: 30.00  flow 45.00   %b: 26.00
     time: 50.00  flow 45.00   %b: 90.00
     time: 55.00  flow 45.00   %b: 26.00
     time: 60.00  flow 45.00   %b: 26.00

Magic Detector
     Run time: 60.00 min
     Deuterium Lamp is Enabled
     Tungsten Lamp is Disabled
     Zero On Change is Enabled
     WaveMode selected: Dual UV (190-365 nm)

Time Program
     time: 0.00   wave1:214   wave2:234
```

FIG. 6A

```
                    LCQ Deca Instrument Method

MS Run Time (min): 60.00

Divert Valve: not used during run

Contact Closure: not used during run

Unimetrics Syringe Settings:

Flow Rate (µL/min): 15.00          Volume (µL): 500.00
Stop Syringe Pump at End of Run: Yes MS Detector Settings:

Real-time modifications to method disabled

Segment 1 Information

Duration (min):          28.34
Number of Scan Events:   4
Tune Method:                    negative ion mode with lc Scan Event Details:
   1:   Neg   o(220.0-400.0)
   2:   Neg   o(220.0-400.0)
   3:   Neg   o(220.0-400.0)
   4:   Neg   o(220.0-400.0)

Segment 2 Information

Duration (min):          31.66
Number of Scan Events:   1
Tune Method:                    angiolowflow Scan Event Details:
   1:   Pos   o(400.0-2000.0)

Custom Data Dependent Settings:
          Not enabled
```

FIG. 6B

```
Duplication of PAL local LC-Inj cycle

Syringe: 10 µL

01 LC-Inj
        Air Volume (µL)                     0
        Pre Clean with Solvent 1            2
        Pre Clean with Solvent 2            3
        Pre Clean with Sample        1
        Filling Speed (µL/s)                .5
        Filling Strokes              5
        Inject to                           LC Vlv1
        Injection Speed (µL/s)       .5
        Pre Inject Delay (ms)        500
        Post Inject Delay (ms)       500
        Post Clean with Solvent 1    3
        Post Clean with Solvent 2    3
        Valve Clean with Solvent 1   3
        Valve Clean with Solvent 2   3

SS420 Board Method

I. Acquisition

1. Number of channel in use: 2
        2. Channel descriptions:
              A: 214
              B: 234
        3. Sampling frequency (Hz): 10.000000
        4. Acquisition time:
              Run in 60.00 min II. External Events:

External Events:  not in use

III. Configuration

Board Number: 1
        Trigger Line: 1
        Trigger type: closed contact causes trigger
```

FIG. 6C

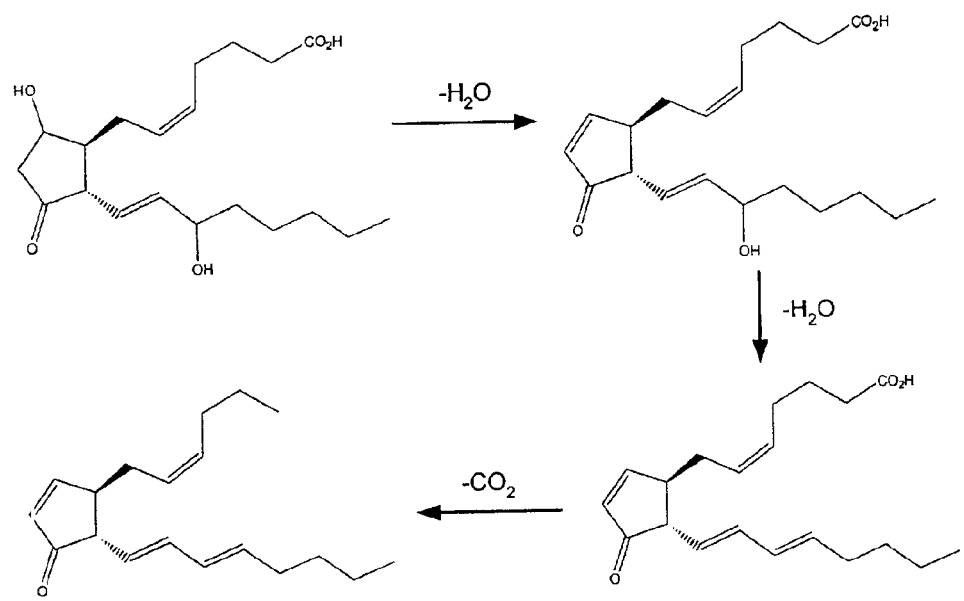
PRIOR ART FIG. 7A
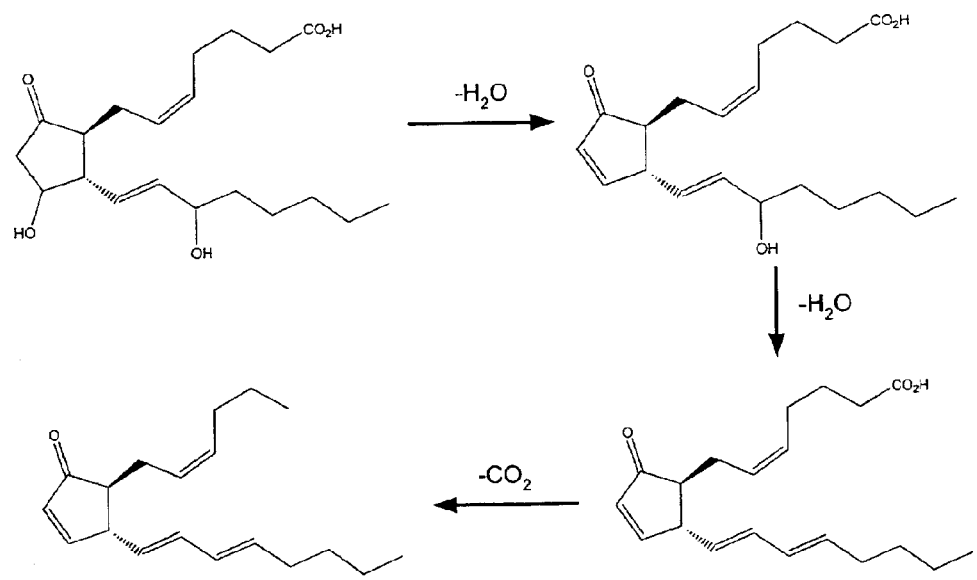
PRIOR ART FIG. 7B

MASS SPECTROMETRY OF PROSTAGLANDINS

RELATED APPLICATIONS

This application claims the benefit of U.S. Provisional Application No. 60/261,577, "Mass Spectrometry of Prostaglandins," filed Jan. 12, 2001, which is herein incorporated by reference in its entirety.

FIELD OF THE INVENTION

The present invention relates generally to the analysis of chemical mixtures. More particularly, it relates to a liquid chromatography-electrospray ionization mass spectrometry method for separating and identifying prostaglandin isomers.

BACKGROUND OF THE INVENTION

Prostaglandins are biologically important metabolites derived from arachidonic acid. FIG. 1 shows schematically the biochemical pathways of arachidonic acid metabolism, indicating the position of the various prostaglandins (PG). As exemplified by the two structures in FIGS. 2A and 2B, prostaglandins are 20-carbon fatty acids that contain a 5-carbon ring. While structurally similar, the molecules are functionally quite diverse. Prostaglandins act as mediators in a large number of physiological processes, including hemostasis and thrombosis, and contribute to pathologic processes associated with inflammation, atherosclerosis, and bronchoconstriction. There is therefore a great deal of interest in elucidating their roles, a process that requires sensitive and specific detection at nanomolar levels in complex biological matrices.

Gas chromatography-mass spectrometry (GC-MS) has been the traditional tool for detecting metabolites in the arachidonic acid pathway. However, these methods require extensive sample preparation and cumbersome derivatization procedures. Several analytical steps are required for extraction, separation, and purification before derivatization and separation by GC-MS. While these techniques have been improved in recent years, they remain costly and laborious and yield variable results. In addition, arachidonyl-derived lipids in biological fluids, particularly plasma, are known to be relatively unstable and undergo a variety of transformations when subjected to harsh derivatization conditions. The samples therefore need to be treated carefully, and antioxidants are commonly used to prevent further oxidation.

Recently, liquid chromatographic techniques have been developed to separate prostaglandin-containing mixtures with minimal sample preparation prior to analysis. When combined with electrospray ionization (ESI) mass spectrometry, LC has picogram detection limits, which is sufficient bioanalytical sensitivity for many applications. Furthermore, MS and tandem MS can often provide necessary structure elucidation to resolve co-eluting species without tedious derivatization and sample manipulation. For example, a method for high performance liquid chromatography/tandem mass spectrometry of $F_2$-isoprostanes is disclosed in H. Li et al., "Quantitative high performance liquid chromatography/tandem mass spectrometric analysis of the four classes of $F_2$-isoprostanes in human urine," Proc. Natl. Acad. Sci. 96, 1999: 13381–13386. While this method is useful for the particular species studied, it cannot be generalized to all prostaglandins. One of the challenges in combining LC and ESI-MS for analyzing prostaglandins is that optimal conditions for one technique are often not ideal for the other. That is, conditions that maximize ionization efficiencies reduce chromatographic separation resolution, while ideal chromatographic conditions lead to poor electrospray ionization efficiencies.

This problem is particularly pronounced for the two prostaglandin isomers illustrated in FIGS. 2A and 2B. Prostaglandin $D_2$ ($PGD_2$) and prostaglandin $E_2$ ($PGE_2$) are isomers having different roles in inflammatory processes. $PGD_2$ is the major eicosanoid product of mast cells and is released during allergic or asthmatic anaphylaxis, while $PGE_2$ activates inflammatory processes and is important in fertility and gastric mucosal integrity. Because of these different functions, it is desirable for researchers to be able to distinguish and quantify the two isomers by LC-MS. For sufficient ionization of the two species, particularly at low concentrations or small sample size, negative ion mode is required, which entails basic solution conditions. Under these conditions, however, the species tend to co-elute from the chromatographic column. Because the two prostaglandin structures are so similar, differing only in the reversed positions of a hydroxyl and carbonyl group, their mass spectra cannot distinguish the co-eluted species. Furthermore, while it is often common to distinguish isomers by their tandem mass spectra (further fragmentation of the parent and subsequent ions), $MS^2$ and $MS^3$ tandem mass spectra of the two species are also virtually identical.

There is a need, therefore, for a LC-MS method for detecting and distinguishing between prostaglandin isomers at low concentrations. It is desirable that the method require little sample preparation and no sample derivatization and be able to detect and distinguish between picogram quantities of different prostaglandins.

SUMMARY OF THE INVENTION

The present invention provides a method for performing liquid chromatography-mass spectrometry on a chemical mixture containing at least two different prostaglandins. The method allows the two species to be separated and identified at very low concentrations, such as nanomolar. The method is performed by conducting a liquid chromatographic separation of the mixture, adding a basic liquid in sheath flow to the eluent, and performing mass spectrometry, preferably using electrospray ionization, on the diluted eluent. The chromatographic separation is performed under acidic conditions to ensure separation of the prostaglandin species, which are preferably $PGD_2$ and $PDE_2$. The basic conditions of the ionization provide for high ionization efficiency in the negative ion mode. Preferably, the mass spectrometry includes $MS^4$, which allows the two isomers to be distinguished.

The present invention also provides a method for distinguishing between at least two prostaglandin isomers, such as $PGD_2$ and $PGE_2$, using tandem mass spectrometry, preferably $MS^4$. The spectra are acquired at different ionization energies, at least one of which is capable of producing spectra that are significantly different from each other. Preferably, the ionization energy is varied until an energy is found at which the spectra are most different from each other, thereby facilitating correct identification of the two prostaglandin isomers.

BRIEF DESCRIPTION OF THE FIGURES

FIGS. 6A–6C show equipment operation and settings used to obtain the chromatogram of FIG. 5.

FIGS. 7A and 7B (prior art) are schematic diagrams of the collision-induced dissociation schemes of $PGD_2$ and $PGE_2$.

DETAILED DESCRIPTION OF THE INVENTION

The present invention provides a liquid chromatography (LC)-electrospray ionization (ESI) mass spectrometry (MS) method for separating and detecting different prostaglandin species. In particular, the two isomers $PGD_2$ and $PGE_2$ can be separated using methods of the invention. Furthermore, based on their tandem mass spectra, the isomers can be distinguished and the identities of the corresponding chromatographic peaks verified. Thus, according to the invention, isobaric prostaglandins $PGD_2$ and $PGE_2$ in biological matrices can be distinguished by capillary $LC-MS^4$ without extensive sample preparation and tedious derivatization. The detection limits of the method approach nanomolar levels when the mass spectrometer is operated in select ion monitoring mode.

According to a method of the invention, solution conditions are implemented that optimize both chromatographic separation and ionization efficiency. Optimized ionization efficiency is particularly important when the analyte of interest is at low concentrations or the available sample volume is small. In order to optimize conditions for both chromatography and spectrometry, the chromatography is performed under acidic conditions to enhance separation, while the spectrometry is performed under basic conditions to increase ionization efficiency in the negative ion mode. This is accomplished by introducing a basic solution between the two stages using a basic sheath flow liquid.

Figure 1:
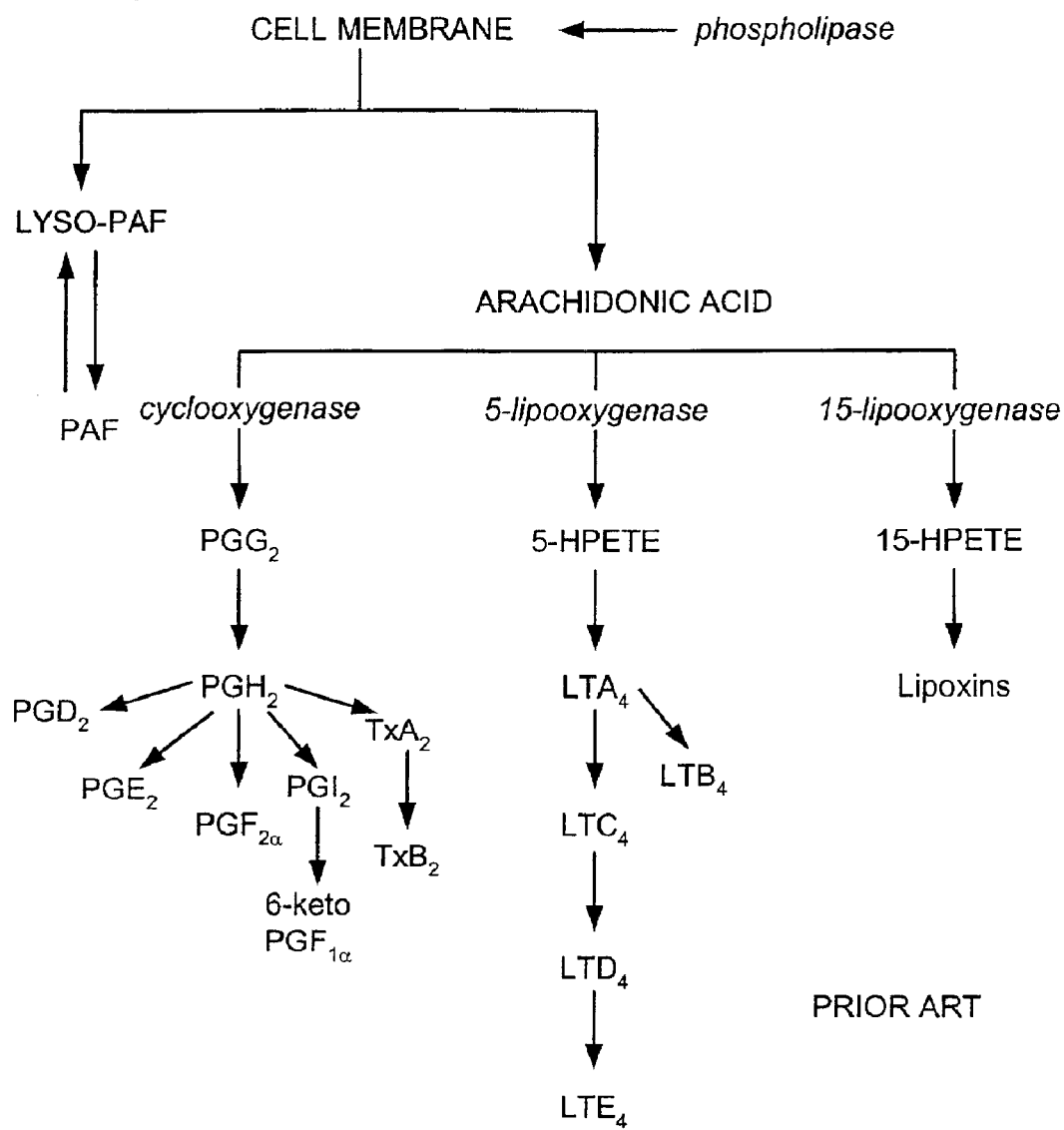
FIG. 1 (prior art) shows the metabolic pathway of arachidonic acid to form prostaglandins.
Figure 2A:
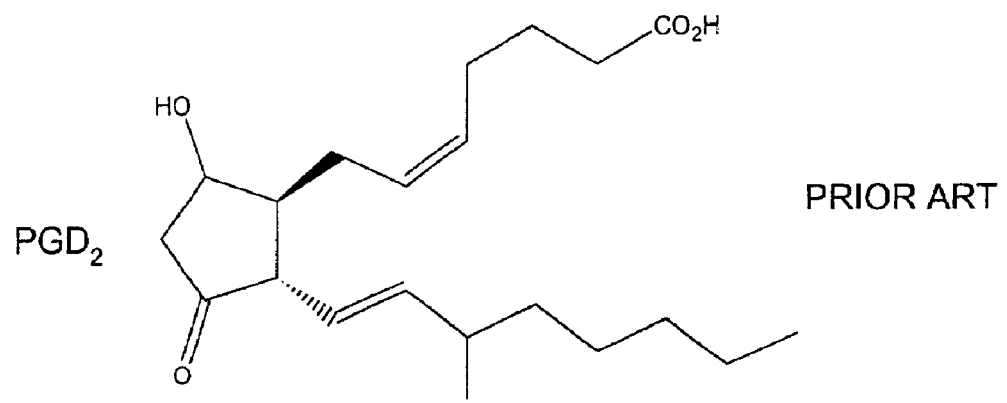
FIGS. 2A and 2B (prior art) show the structures of prostaglandins $D_2$ and $E_2$.
Figure 2B:
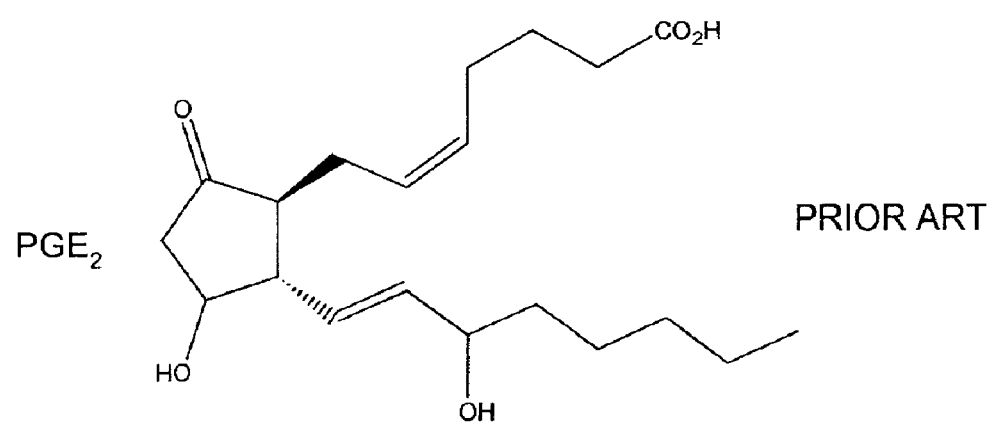
Figure 3:
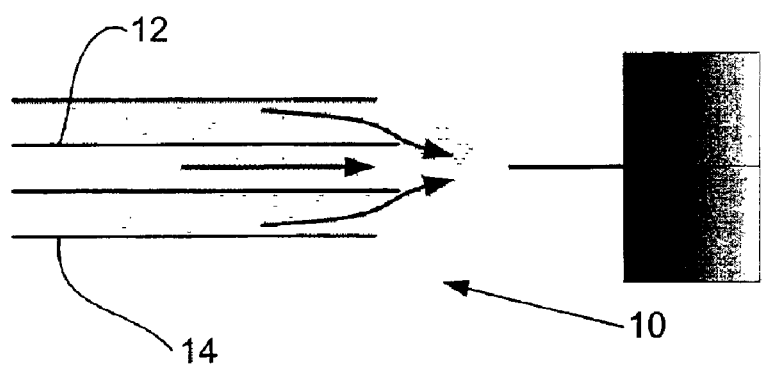
FIG. 3 is a schematic diagram of an interface between a chromatography column and an electrospray needle illustrating sheath flow according to the present invention.

FIG. 3 illustrates a portion 10 of a combined LC/MS instrument of the invention showing the end of a chromatographic column 12 and stainless steel tube 14, which together form an electrospray ionization needle. An additional solution is introduced into the eluent using the tube 14, which acts as a sheath surrounding the chromatographic column. For this reason, the additional solution is referred to as being in sheath flow. In a preferred embodiment, the sheath liquid is a basic solution. For example, the sheath liquid can be ammonium hydroxide in a solution of methanol and acetonitrile. In general, the sheath liquid is sufficiently volatile to be used in electrospray ionization and has a pH that provides for an ionization efficiency that is at least sufficient for the prostaglandins to be detected. The specific characteristics of a suitable sheath liquid depend upon features of the particular experiment, including the instrument and sample components. Because the sheath flow is introduced only after the chromatographic separation, it has no effect on the separation, and separation can occur under acidic conditions that are effective for providing a satisfactory resolution of the prostaglandin species. Suitable chromatographic solvents depend upon the particular conditions and should allow for sufficient separation resolution and ionization. For example, the solvents can be mixtures of acetic acid, heptafluorobutyric acid, and acetonitrile.

Figure 4:
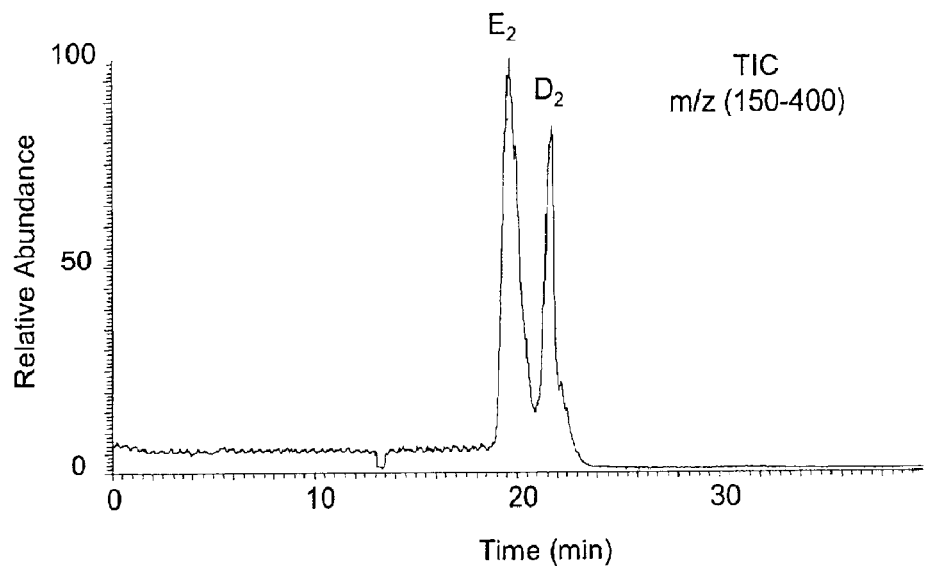
FIG. 4 is a total ion current chromatogram of a $PGD_2$ and $PGE_2$ mixture obtained using the LC-ESI MS instrument of FIG. 3.

FIG. 4 shows a total ion current chromatogram obtained from a LC-ESI MS analysis of a mixture of $PGD_2$ and $PGE_2$. In this particular example, the capillary column used was a 0.2×150 mm Magic C18 column (Michrom BioResources, Auburn, Calif.) with 5 µm 200 Å packing. Solvent A was 2% acetonitrile and 98% water containing 0.4% acetic acid and 0.005% heptafluorobutyric acid. Solvent B was 90% acetonitrile and 10% water containing 0.005% heptafluorobutyric acid. Isocratic separation was performed with 26% solvent B at a flow rate of 4 µL/min. The sample concentration was 1 ng/µL and the injection volume 2 µL. The eluent was combined with a sheath liquid of 0.1% $NH_4OH$ in a solution of 50% methanol and 50% acetonitrile. As further confirmed by mass spectrometry (discussed below), the $PGD_2$ and $PGE_2$ peaks were well separated. Note that the specific details listed are for illustration purposes only and in no way limit the scope of the invention.

Figure 5:
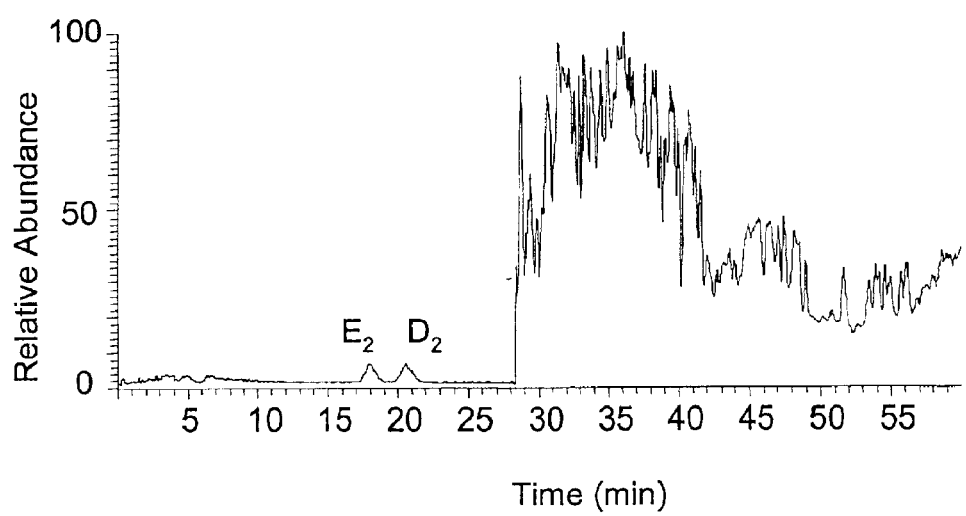
FIG. 5 is a total ion current chromatogram of a human plasma fraction spiked with $PGD_2$ and $PGE_2$ obtained using the LC-ESI MS instrument of FIG. 3.

The LC-MS separation was also performed when the prostaglandins were added to a human plasma fraction from which human serum albumin and proteins with molecular weight greater than 10 kDa were removed. The total ion current (TIC) chromatogram for this mixture is shown in FIG. 5. In this example, capillary liquid chromatography was performed using a MAGIC 2002 system (Michrom BioResources, Auburn, Calif.) and mass spectrometry with a Finnigan LCQ Deca (ThermoFinnigan, San Jose, Calif.). The chromatographic column was a Magic C18 reversed phase silica column (Michrom) with a 5 µm particle size and 200 Å pore size. Relevant instrument settings are shown in FIGS. 6A–6C.

In this example, the plasma fraction was spiked with $PGD_2$ and $PGE_2$ at a concentration of 50 pg/µL of each prostaglandin. 2 µL of this solution was injected and analyzed. Solvents A and B were as described above for FIG. 4. The separation was performed isocratically with 26% solvent B at 4 µL/min with a sheath liquid of 0.1% $NH_4OH$ in a 50:50 mixture of methanol and acetonitrile. As shown in FIG. 5, physiologically relevant concentrations of $PGD_2$ and $PGE_2$ can be detected using the method of the invention under these conditions.

The present invention also includes methods for distinguishing between prostaglandin isomers using tandem mass spectrometry. FIGS. 7A and 7B show collision-induced dissociation schemes for the $D_2$ and $E_2$ prostaglandin isomers. Note that the sequential generations of ion fragments for the two species have identical masses. Tandem mass spectrometry performed by the present inventors on both isomers yields a parent ion $[M-H]^-$ at a mass-to-charge ratio (m/z) of 351.2, an $MS^2$ ion $[M-H-H_2O]^-$ at an m/z of 333.3, an $MS^3$ $[M-H-2H_2O]^-$ at an m/z of 315.2, and an $MS^4$ ion $[M-H-2H_2O-CO_2]^-$ at an m/z of 271.3. Thus the standard method of obtaining multiple tandem mass spectra to distinguish isomers is not applicable to separating $PGD_2$ and $PGE_2$.

Although the two isomers follow the same overall dissociation scheme, the different ions generated have different relative energies. For a given ionization energy input, therefore, the extent of dissociation is different for the two isomers. Thus according to the present invention, the two isomers can be distinguished based on the different amounts of dissociation at one or more different energy inputs. ESI in the negative ion mode followed by fragmentation of the parent ions in an ion trap to yield $MS^2$, $MS^3$, and $MS^4$ spectra has been used by the present inventors to distinguish the isobaric species in a mixture. The $MS^2$ spectra and $MS^3$ spectra were essentially identical for the two species at all ionization energies.

Figure 8A:
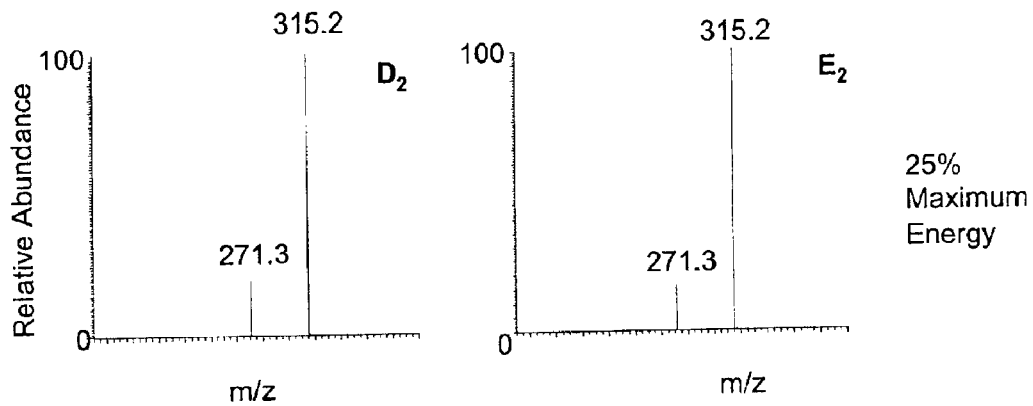
FIGS. 8A–8C are $MS^4$ spectra of $PGD_2$ and $PGE_2$ at three different ionization energies.
Figure 8B:
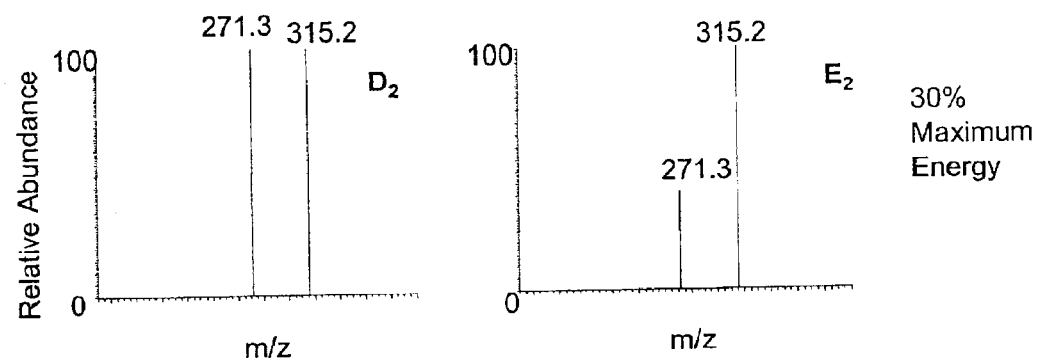
Figure 8C:
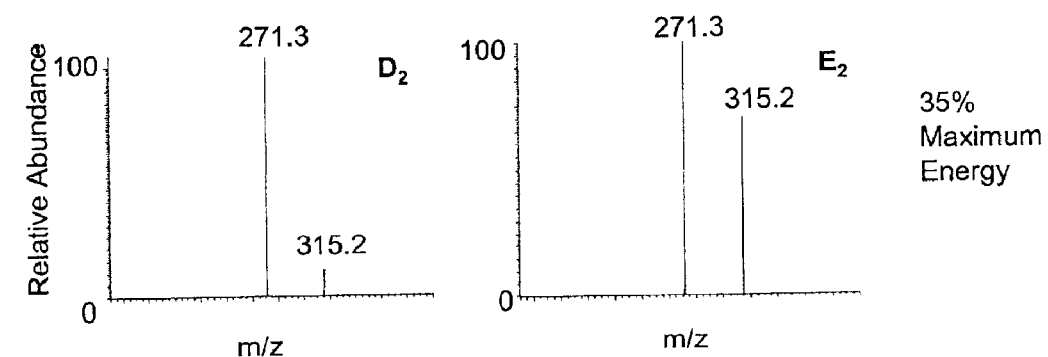

However, the $MS^4$ spectra varied at some of the ionization energies. Three different $MS^4$ spectra for each of the two isomers at three different ionization energies are shown in FIGS. 8A–8C. FIG. 8A shows the spectra for an ionization energy of 25% of the total available instrument energy. Both spectra show a peak at m/z=315.2 and m/z=271.3. The relative heights of the two peaks are substantially equivalent in the two spectra, making the spectra virtually indistinguishable and not useful for identifying the prostaglandin isomers. However, when the ionization energy is increased, the relative heights of the two peaks are significantly different. FIG. 8B shows the spectra at a slightly increased ionization energy of 30%, and FIG. 8C at 35%. Although relative ion abundances are known to fluctuate quite significantly for electrospray ionization, typically on the order of 10%, the differences in peak heights between the two spectra is sufficient, even with a 10% fluctuation, to distinguish the spectra in both of these cases. These spectra are referred to as significantly different from each other. At 30%, there is a greater extent of dissociation of the $MS^3$ ion (m/z=315.2) of prostaglandin $D_2$ than of $E_2$, and at 35%, there is an even greater difference in the relative extents of dissociation.

The optimal ionization energies for distinguishing between isomers cannot be determined a priori but must be identified empirically. In addition, the optimal energy fluctuates with instrument and must be determined separately for each instrument. Preferably, the ionization energy is adjusted until the energy at which the two spectra are most different is determined. This energy can then be used for subsequent experiments.

It should be noted that the foregoing description is only illustrative of the invention. Various alternatives and modifications can be devised by those skilled in the art without departing from the invention. Accordingly, the present invention is intended to embrace all such alternatives, modifications and variances which fall within the scope of the disclosed invention.

What is claimed is:

1. A method for performing liquid chromatography-mass spectrometry on a chemical mixture comprising at least two prostaglandins, said method comprising:

a) performing a liquid chromatographic separation of said mixture under acidic conditions, thereby generating an eluent;

b) using sheath flow, adding a basic liquid to said eluent to generate a diluted eluent; and c) performing mass spectrometry on said diluted eluent.

2. The method of claim 1, wherein said prostaglandins are PGD2 and PGE2.

3. The method of claim 1, wherein performing said mass spectrometry comprises ionizing said diluted eluent by electrospray ionization.

4. The method of claim 1, wherein performing said mass spectrometry comprises performing tandem mass spectrometry.

5. The method of claim 4, wherein said tandem mass spectrometry comprises MS4.

6. The method of claim 1, wherein said prostaglandins are isobaric.

7. The method of claim 1, wherein said prostaglandins are isomers.

8. The method of claim 1, wherein performing said mass spectrometry comprises performing mass spectrometry in the negative mode.

9. The method of claim 1, wherein the basic liquid comprises ammonium hydroxide.

10. The method of claim 1, wherein the basic liquid comprises acetonitrile.

11. The method of claim 1, wherein the eluent comprises acetic acid.

12. The method of claim 1, wherein the eluent comprises acetonitrile.

13. A method for performing liquid chromatography-mass spectrometry on a chemical mixture comprising at least two prostaglandins, said method comprising:

a) performing a liquid chromatographic separation of said mixture under acidic conditions, thereby generating an eluent;

b) using sheath flow, adding a basic liquid to said eluent to generate a diluted eluent; and c) performing tandem mass spectrometry on said diluted eluent.

14. The method of claim 13, wherein said prostaglandins are $PGD_2$ and $PGE_2$.

15. The method of claim 13, wherein performing said mass spectrometry comprises ionizing said diluted eluent by electrospray ionization.

16. The method of claim 13, wherein said liquid chromatographic separation is performed under acidic conditions.

17. The method of claim 13, wherein said tandem mass spectrometry comprises $MS^4$.

18. The method of claim 13, wherein said prostaglandins are isobaric.

19. The method of claim 13, wherein said prostaglandins are isomers.

20. The method of claim 13, wherein performing said mass spectrometry comprises performing mass spectrometry in the negative mode.

21. The method of claim 13, wherein the basic liquid comprises ammonium hydroxide.

22. The method of claim 13, wherein the basic liquid comprises acetonitrile.

23. The method of claim 13, wherein the eluent comprises acetonitrile.

* * * * *